(12) United States Patent
Boden et al.

(10) Patent No.: US 7,468,447 B1
(45) Date of Patent: Dec. 23, 2008

(54) REGIOSPECIFIC FURAN COMPOUNDS AND THEIR USE IN FRAGRANCES

(75) Inventors: Richard Boden, Ocean, NJ (US); Paul Daniel Jones, Matawan, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 11/942,020

(22) Filed: Nov. 19, 2007

(51) Int. Cl.
*C07D 307/92* (2006.01)

(52) U.S. Cl. .......................... 549/458; 512/13

(58) Field of Classification Search ................. 549/458; 512/13
See application file for complete search history.

(56) References Cited

OTHER PUBLICATIONS

Arctander, Perfume and Flavor Chemicals (Aroma Chemicals) I,Published by The Author Montclair, N. J. (USA), compound 1213 and p. I of Table No. 1 (1969).*

Grossman et al, Proceedings of VII Symposium of IUPAC and Chemistry of Natural Substances, published Riga, Latvia, p. 494-495 (1970).*

\* cited by examiner

*Primary Examiner*—Bernard Dentz
(74) *Attorney, Agent, or Firm*—Elizabeth M Quirk; Joseph F. Leightner; Xufan Tseng

(57) ABSTRACT

The present invention is directed to the diastereoisomeric mixture and the individual isomeric components of the formula:

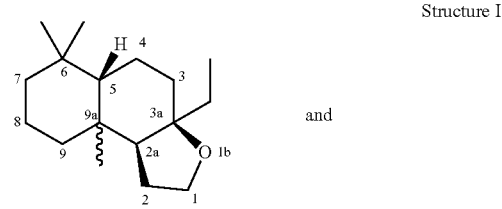

Structure I and

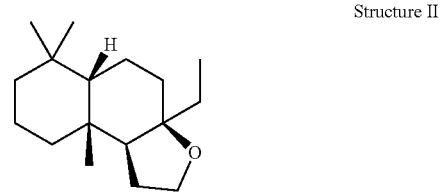

Structure II

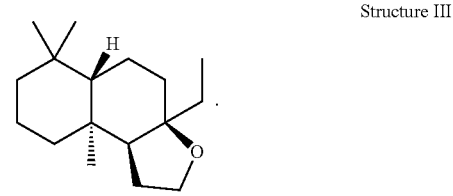

Structure III

3 Claims, No Drawings

REGIOSPECIFIC FURAN COMPOUNDS AND THEIR USE IN FRAGRANCES

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow perfumers to apply the new compounds in creating new fragrances.

One of the aims of the man skilled in the art of perfumery is to find new chemicals with improved performance than prior known compounds from an olfactive point of view, either because their odor qualities are more distinctive and original or because their odor is much stronger or yet, if he is lucky, as a result of both of these. Such a skilled man knows well enough that he cannot rely on structural closeness to predict whether a new chemical will be a more interesting fragrance ingredient or, even, whether it will be fragrant at all. Although he cannot be unaware of the role that the optical isomerism of a compound plays in determining its odor properties or, rather, its odor perception by the perfumer [see, for instance, W. Pickenhagen, in ACS Symposium Series 388, chapter 12, p. 151, ed. ACS, Washington D.C. (1989)], he often finds no motivation to prepare the optically active isomers, particularly when confronted with racemic compounds which possess a plurality of chiral centers, knowing that his task will be extremely difficult and unobvious, as the synthesis of the corresponding pure optical isomers not only requires particular expertise but is also costly. In addition, he may find no reward, as there is no way of predicting, even in the presence of a good racemate, whether his efforts will lead only to the discovery that none of the pure optically active components of said racemate is in any way superior to the latter, as a fragrance ingredient or, at least, not superior enough to justify its inevitably dearer industrial development.

In spite of such difficulties, the synthesis of novel chiral perfuming ingredients is an ever increasing need in this industry. The reason for this springs in an obvious manner from articles such as that of G. Ohloff in Experientia 42, 271 (1986), wherein the author not only impresses upon its reader the importance of every new discovery of fragrant chemicals towards completing an empirically set list of structural conditions or parameters, amongst which chiral activity, disclosed in this article and believed to influence odor perception, but also acknowledges the transient quality, at the present stage of the art, of such lists of structural parameters which, as he admits, every new compound behaving uncharacteristically may well contradict, leading to replacements or alterations. Yet, despite the necessity to continue preparing optically active species of known racemates, the outcome of such an endeavour is rendered all the more uncertain and unobvious by the fact that a racemate does not generally produce a fragrance effect which corresponds to a sum of the individual odor properties of the different optically active isomers present in the racemic mixture, both qualitatively and quantitatively, and this even when there are only two of such isomers in said mixture. The olfactive properties of the racemate can be, and often are, quite different from those of each optically active component of said racemate and, that is why it is impossible to predict the olfactive behaviour of any one isomer on the basis of the knowledge of the racemate, particularly when, as is the case here, there are several optically active isomers in the racemic mixture. The result of the chemist's research in this domain is therefore unpredictable.

It should be further noted that in the present case, the individual optically active isomers cannot be simply separated from the known racemic mixtures, but require specifically designed and sophisticated syntheses, as described further on.

The present invention is yet another example of this reality and it brings precisely a new and unexpected contribution into this field.

SUMMARY OF THE INVENTION

The present invention is concerned with the Diastereoisomeric mixture of the Structure I:

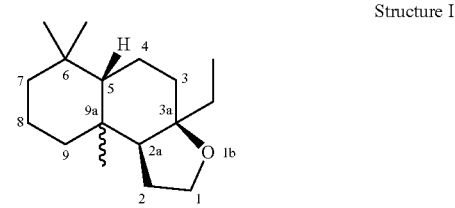

Structure I

In accordance with the invention, a stereoselective process is disclosed for synthesizing the diastereoisomeric mixture of Structure I and the individual isomeric components of the following compounds:

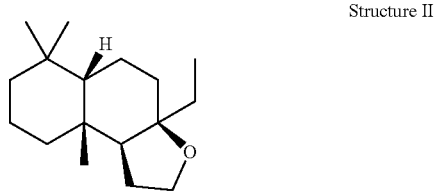

Structure II cis

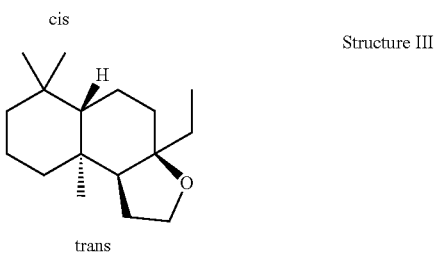

Structure III trans

Additionally, the invention concerns odorant compositions containing Structure I and the use of Structure I as an odorant.

In yet a further embodiment, the invention concerns odorant compositions containing either Structure II and Structure III and the use of Structure II and Structure III as individual odorants.

DETAILED DESCRIPTION OF THE INVENTION

It has been surprisingly discovered that the optically active isomers and isomeric mixtures of the present invention possess superior organoleptic properties. In addition, the optically active isomers are distinctly advantageous in perfumery applications when compared to their racemic mixture counterparts known from the prior art.

The process known in the art to make the compound commercially known as Grisalva was not regiospecific, thus Grisalva was comprised of approximately 14 different components. Grisalva is commercially available from International Flavors & Fragrances Inc. In our improved process we have surprisingly found a regiospecific ring forming procedure which produces the high purity diastereomeric mixture and the individual isomeric components.

Structure II and III are accessible according to the following Scheme:

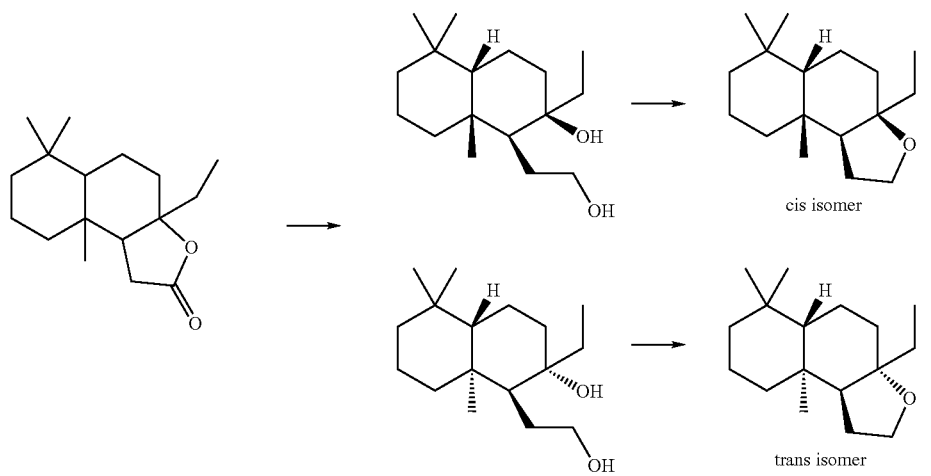

The individual steps involved in the process are based on chemistry known to one skilled in the art.

According to one of the embodiment of the invention, the preparation of an Diastereoisomeric mixture of the structure, known by one skilled the art known by one skilled in the art as 3a-Ethyl-6,6,9a-trimethyl-dodecahydro-napthol[2,1-b]furan:

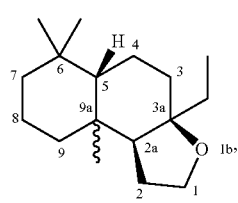

is prepared according to the following steps:

(1) Subjecting a compound of Structure IV, known by one skilled in the art as 1-(2,2,6-Trimethyl-cyclohexyl)-pentan-3-one,

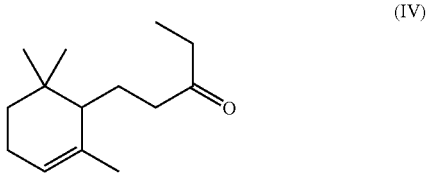

(IV)

to Darzen's condensation to provide a compound of Structure V, 3-Ethyl-3-[2-(2,6,6-trimethyl-cyclohex-2-enyl)-ethyl]-oxirane-2-carboxylic acid methyl ester

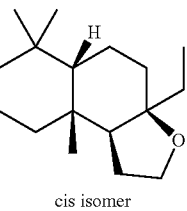

(V)

(2) saponifying the compound of Structure V to provide a compound of Structure VI, known by one skilled in the art as 3-ethyl-3-[2-(2,2,6-trimethyl-cyclohexyl)-ethyl]-oxirane-2-carboxylic acid,

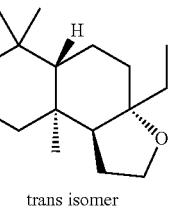

(VI)

(3) subjecting the compound Structure VI to pyrolysis to provide a compound of Structure VII 2-ethyl-4-(2,6,6-trim-ethyl-cyclohex-2-enyl)-butyraldehyde]

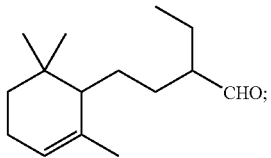

(VII)

(4) subjecting a compound of structure VII to Knoevenagel reaction with cyanoacetic acid to provide a compound of structure VIII 4-ethyl-6-(2,6,6-trimethylcyclohex-2-enyl) hex-3-enenitrile

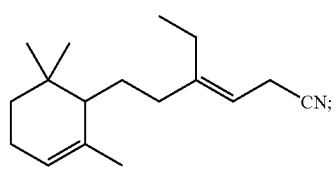

(VIII)

(5) providing a compound of structure IX, known by one skilled in the art as 2-ethyl-5,5,8a-trimethyl-3,4,4a,5,6,7,8, 8a-octahydro-naphthalen-1-yl)-acetonitrile by subjecting structure VIII to ring closing reaction

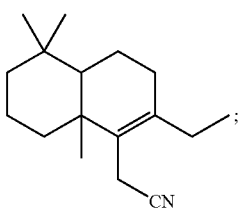

(IX)

(6) saponifying the compound of structure IX to provide a compound of structure X, known by one skilled in the art as 2-ethyl-5,5,8a-trimethyl-3,4,4a,5,6,7,8,8a-octahydro-naph-thalen-1-yl)-acetic acid,

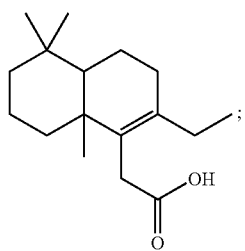

(X)

(7) cyclizing the compound of structure X to provide a compound of structure XI, known by one skilled in the art as 3a-Ethyl-6,6,9a-trimethyl-decahydro-naphthol[2,1-b]furan-2-one,

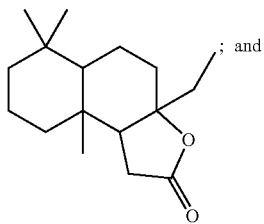

(XI)

(8) reducing the compound of structure XI to provide the structure XII, known by one skilled in the art as 2-ethyl-1-(2-hydroxy-ethyl)-5,5,8a-trimethyl-decahydro-napthalen-2-ol,

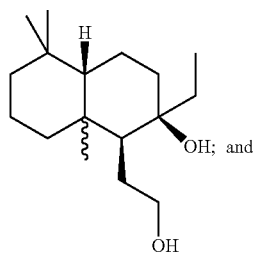

(XII)

(9) subjecting structure XII to ring closing reaction to provide the diastereoisomeric mixture of structure I:

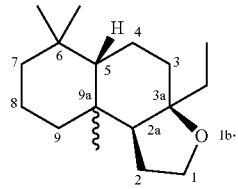

According to another embodiment of the invention, the individual isomeric components are obtained following the process detailed below:

(1) subjecting a compound of structure IV

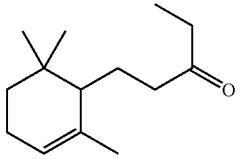

(IV)

to Darzen's condensation to provide a compound of Structure V, 3-Ethyl-3-[2-(2,6,6-trimethyl-cyclohex-2-enyl)-ethyl]-oxirane-2-carboxylic acid methyl ester

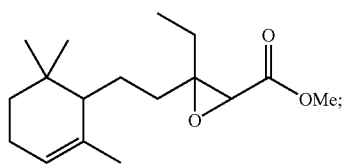

(V)

(2) saponifying the compound of Structure V to provide a compound of Structure VI, known by one skilled in the art as 3-ethyl-3-[2-(2,2,6-trimethyl-cyclohexyl)-ethyl]-oxirane-2-carboxylic acid,

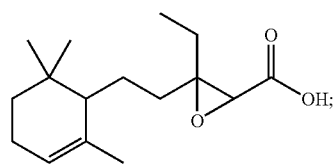

(VI)

(3) subjecting the compound Structure VI to pyrolysis to provide a compound of Structure VII 2-ethyl-4-(2,6,6-trimethyl-cyclohex-2-enyl)-butyraldehyde

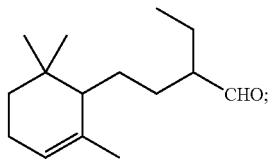

(VII)

(4) subjecting a compound of structure VII to Knoevenagel reaction with cyanoacetic acid to provide a compound of structure VIII, 4-ethyl-6-(2,6,6-trimethylcyclohex-2-enyl) hex-3-enenitrile

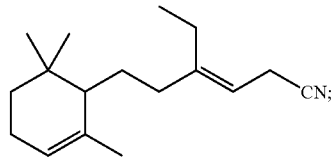

(VIII)

(5) providing a compound of structure IX, known by one skilled in the art as 2-ethyl-5,5,8a-trimethyl-3,4,4a,5,6,7,8,8a-octahydro-naphthalen-1-yl)-acetonitrile by subjecting structure VIII to ring closing reaction

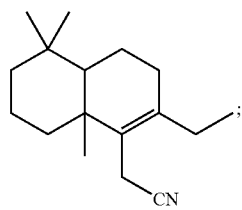

(IX)

(6) saponifying the compound of structure IX to provide a compound of structure X

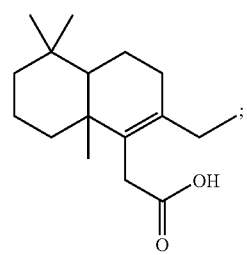

(X)

(7) cyclizing the compound of structure X to provide a compound of structure XI

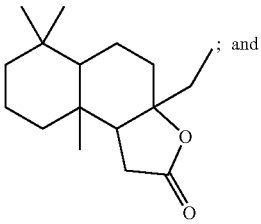

(XI)

; and (8) reducing the compound of structure XI to provide structure XII

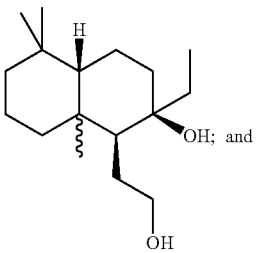

(XII)

; and (9) crystallizing the compound of structure XII to form crystals and collecting the crystals via vacuum filtration and subjecting the crystals to a ring closure reaction and obtaining the cis isomer of Structure II, (3aR,5aS,9aR,9bS)-3a-ethyl-6,6,9a-trimethyldodecahydronaphtho[2,1-b]furan

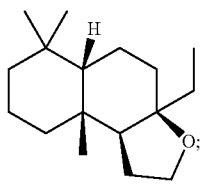

(10) the remaining sample containing structure XII was heated, then cooled to room temperature and was seeded with the crystals collected in the earlier filtration. The crystals that formed were collected via vacuum filtration and the crystals were subjected to ring closure and the trans isomer of Structure III was obtained: (3aR,5aS,9aS,9bS)-3a-ethyl-6,6,9a-trimethyldodecahydronaphtho[2,1-b]furan

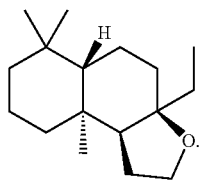

It is a matter of course that modifications concerning the reagents and reaction conditions are possible.

According to one embodiment of the invention, it has been found that the novel compounds possess valuable odorant properties and can accordingly be used as odorants. The olfactory notes of Structure I can be characterized as possessing nice woody, amber and flowery notes, Structure II possesses woody, labdanum and ambergris notes and Structure a III possesses woody, ambery ionone and strong fragrance notes.

On the basis of their olfactory notes, Structure I and the individual isomers, Structure II and III, are especially suitable for modifying and intensifying known compositions. In particular, their extraordinary olfactory strength, which contributes quite generally to the refinement of the compositions, should be emphasized. The diastereoisomeric mixture may have a geometrical isomer purity of at least about 90%, preferably of at least about 95%, more preferably of at least about 97.5% and most preferably of at least about 99%. Each of the individual components may have a geometrical isomer purity of at least about 90%, preferably of at least about 95%, more preferably of at least about 97.5% and most preferably of at least about 99%.

A fragrance composition is also provided containing a fragrance-enhancing amount of the Structure I, II or III wherein the compound has a geometrical isomer purity of at least about 90%, preferably a geometrical isomer purity of at least about 95%, more preferably a geometrical isomer purity of at least about 97.5% and most preferably a geometrical isomer purity of at least about 99.5%.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million and g is understood to be grams. All U.S. patents mentioned above are incorporated herein by reference. IFF as used in the examples is understood to mean International Flavors & Fragrances Inc., New York, N.Y., USA. All fragrance materials mentioned in the examples are available from IFF.

EXAMPLE I

Preparation of the Diastereoisomeric Mixture and the Individual Isomeric Components Step 1: Darzen's Condensation

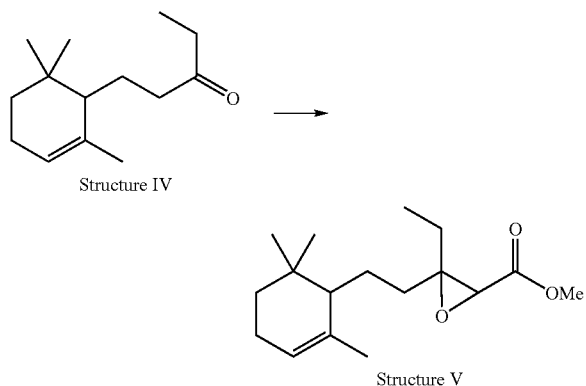

Structure IV

Structure V

Procedure:

To a 5 L flask under nitrogen was added toluene (1 L) and potassium tert-butoxide (336 g), and the stirred mixture was cooled to −10° C., Dihydromethyl ionone (582 g) was charged over 10 minutes while maintaining a temperature between −10° C. and 0° C. Methyl chloroacetate (313 g) was charged over 4 hours such that the internal temperature did not exceed 0° C.

The reaction stirred for an additional 1.5 hours while warming to room temperature (GC indicated an 80% conversion) and the reaction was quenched by the addition of 2 L 3% acetic acid solution. The layers were separated, and the organic layer was washed with water until neutral prior to purification via rushover distillation.

The crude ester was purified by distillation using a rushover apparatus consisting of a 3 L distillation flask equipped with a 2 inch splash column containing stainless steel mesh, a rushover column, and a fraction cutter. The material was distilled with 25 g of primol.

Step 2: Saponification of Glycic Ester

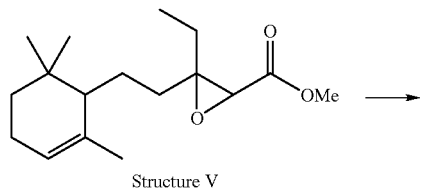

Structure V

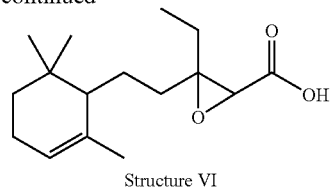

Structure VI

Procedure:

The ester (1014 g) and methanol (2 L) was charged under nitrogen to a 5 L flask, and the reaction was cooled to 0-5° C. Sodium hydroxide was fed over 15 minutes (exothermic) such that the reaction temperature did not exceed 20° C. The reaction was stirred at room temperature for 2 hours and was poured into water (2 L) and toluene (800 mL)—the mixture was stirred and the organic layer was discarded. The aqueous layer was extracted with toluene (800 mL)—discard organic layer. The aqueous layer was returned to the reaction flask and was cooled to 5° C. Phosphoric acid was fed into the stirred solution (exothermic) over 15 minutes such that the reaction temperature did not exceed 20° C. The crude reaction mixture was poured into a separatory funnel and the layers were separated.

Step 3: Pyrolysis of Carboxylic Acid

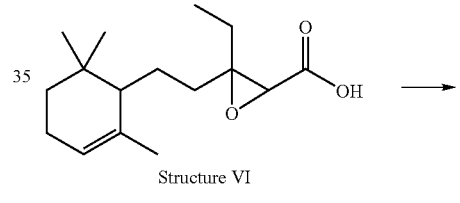

Structure VI

Structure VII

Procedure:

Primol was added to the 3 L flask and the system was placed under vacuum (5-9 mm Hg).

After heating the primol to 210° C., the crude acid mixture was fed into the primol over 6.5 hours—product distills during feed. After the feed was complete, the vacuum was increased to 1.5 mm Hg and held for 15 minutes. The distilled mixture was washed with saturated sodium bicarbonate, then brine and was purified by rushover distillation.

The crude aldehyde was purified by distillation using a rushover apparatus consisting of a 2 L distillation flask equipped with a 2" splash column containing stainless steel mesh, a rushover column, and a fraction cutter.

Step 4: Knoevenagel Reaction

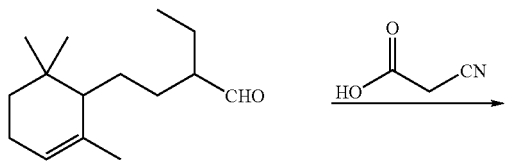
Structure VII

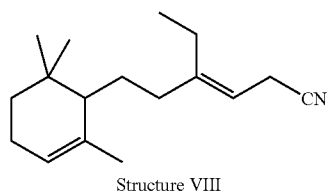
Structure VIII

Procedure:

The aldehyde was charged, under nitrogen, to the 3 L reaction flask followed by cyanoacetic acid, DMF, 2-ethylhexylamine, and acetic acid. With stirring, the mixture was placed under vacuum (120 mm) and was heated to 80-85° C. Note: Cyanoacetic acid begins to decompose near 90° C. During the reaction, water and some DMF distilled from reaction. When the distillation ended (35 minutes), the vacuum was increased to 70 mm, and the reaction stirred for an additional 30 minutes (additional water distilled from the reaction)-check for remaining starting material (GC). Note: Do not raise temperature above 85° C., as cyanoacetic acid will begin to decompose near 90° C. Additional cyanoacetic acid, 2-ethylhexylamine, and acetic acid (0.1 eq each) may be added. The reaction was removed from vacuum, the rushover apparatus was removed, a 12 inch reflux column connected to a gas bubbler was attached, and acetic anhydride was added. The reaction was heated to 130° C., and a vigorous evolution of $CO_2$ was observed. After $CO_2$ evolution stopped (2 h), the temperature was raised to 140° C. and the reaction stirred for an additional 30 minutes or until additional $CO_2$ evolution stopped. The reaction was cooled to 50° C., poured into 500 mL water, was stirred and the layers were separated (pH aq=5-6).

The aqueous layer was extracted with saturated sodium bicarbonate (200 mL), and the crude product was purified by fractional distillation.

The crude nitrile was purified by fractional distillation using a 24 inch goodloe-packed column. The material was distilled with 101 g of primol.

Step 5: Phosphoric Acid Catalyzed Ring Closure

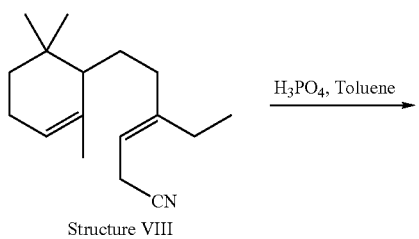
Structure VIII

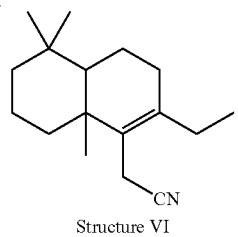
Structure VI

Procedure:

The nitrile was charged under nitrogen to a 2 liter flask followed by toluene and phosphoric acid. The reaction was heated to reflux and stirred for 2 hours, after which time, 450 mL toluene was removed via bidwell. The reaction was cooled to 50° C., poured into water (1 L) and toluene (250 mL), and was stirred and the layers were separated. The aqueous layer was extracted with toluene (250 mL) and the combined organics were washed with saturated sodium bicarbonate, then brine. Solvent was removed via Rot-o-vap (80° C., 40 mm), and the crude bicyclic nitrile was used in the next step without further purification.

Step 6: Saponification of Nitrile to Acid

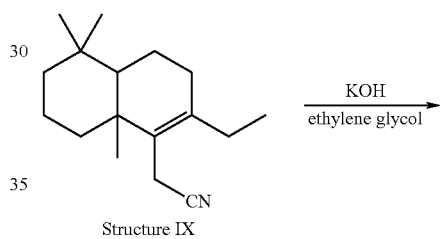
Structure IX

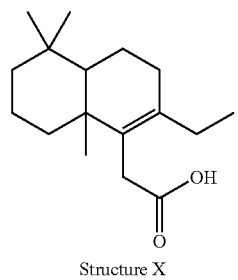
Structure X

Procedure:

The bicyclic nitrile was charged under nitrogen to a 3 L flask followed by ethylene glycol and potassium hydroxide, and was heated to reflux for 4.5 hours.

Reflux began at 150° C., however as water vapor is released through the condenser, the reaction temperature increased to approx. 170° C. The reaction was cooled, poured into water (1.5 L) and toluene (750 mL), was stirred, the layers were separated and the organic layer was discarded. The aqueous layer was extracted with toluene (250 mL×2)—discard organics. The aqueous layer was acidified with hydrochloric acid (conc.) to a pH of 1, and was extracted with toluene (750 mL, then 250 mL). The combined organics were dried via azeotropic distillation using a 3 L 3-neck flask fitted equipped with a mechanical stirrer, heating mantle, thermocouple, a 12" reflux condenser, and a bidwell. The crude solution of product in toluene was used without further purification in the next step.

Step 7: Amberlyst-15 Catalyzed Cyclization of Acid (BC Ring)

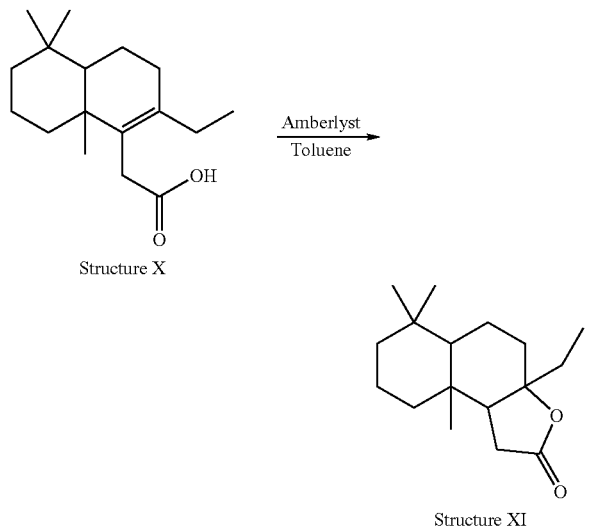

Structure X

Structure XI

Procedure:

The toluene solution of the bicyclic acid was charged under nitrogen to a 3 L flask, Amberlyst-15 was added, the reaction was heated to reflux for 10 hours. The reaction was cooled and filtered, and the Amberlyst resin was washed with toluene (250 ml). Solvent was removed via Rot-o-vap (80° C., 40 mm), and the crude Grisalva lactone was purified by rushover distillation.

The crude lactone was purified by distillation using a rushover apparatus consisting of a 500 mL distillation flask equipped with a 2 inch splash column containing stainless steel mesh, a rushover column, and a fraction cutter, no cooling water was added to the condensor.

Reduction of Lactone to Diol

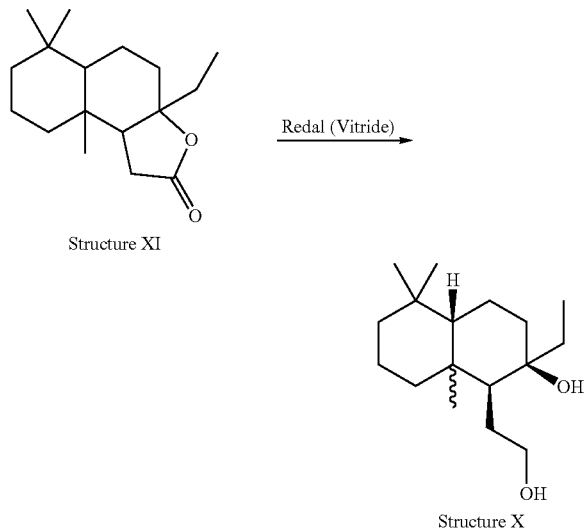

Structure XI

Structure X

Toluene (1794 g) and lactone were charged under nitrogen to a 5 L flask, and the resulting solution was heated to 80° C. Vitride was fed over 1 hour (exothermic) while maintaining 80° C., and the reaction stirred for an additional 2 hours. The reaction temperature was cooled to 75° C., and ethyl acetate was added (mild exotherm). The reaction stirred at 75° C. for 30 minutes, and a preheated 75° C. solution of 2.5% sodium hydroxide (1 L) was added. The reaction was stirred for 1 hour and the layers were separated. The organic layer was washed with hot water (500 mL×3) until the pH of the water wash was 7.5. The crude product in toluene was dried via azeotropic distillation using a 5 L 3-neck flask equipped with a mechanical stirrer, heating mantle, thermocouple, a 12 inch reflux condenser, and a bidwell. The crude reaction product was subjected to ring closure and the resulting mixture was confirmed by GC.

The diastereomeric mixture possesses nice woody, amber and flowery notes.

Isolation of the Isomeric Components

Approximately 100 mL solvent removed during this procedure. The material cooled to room temperature and stood for 12 hours (overnight). The crystals that had formed were collected via vacuum filtration to give 110 g (after drying) rigid, colorless needles that were sparingly soluble in toluene. The crystals were subjected to ring closure and the resulting ether had the same GC retention time as cis isomer of Grisalva. The stereochemistry of the diol collected and the ether formed were therefore assigned as:

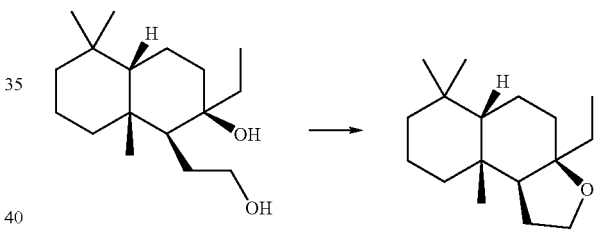

The cis isomer of Structure II possesses woody, labdanum and ambergris notes.

HMNR 0.82 ppm (s, 3H); 0.88 ppm (t, 3H); 0.89 ppm (s, 3H); 1.10 ppm (s, 3H); 1.23 ppm (m, 1H); 1.25 ppm (m, 1H); 1.32 ppm (m, 1H); 1.32 ppm (m, 1H); 1.40 ppm (m, 1H); 1.42 ppm (m, 1H); 1.43 ppm (m, 1H); 1.43 ppm (m, 1H); 1.53 ppm (m, 1H); 1.60 ppm (m, 1H); 1.65 ppm (m, 1H); 1.67 ppm (m, 1H); 1.67 ppm (m, 1H); 1.72 ppm (m, 1H); 1.83 ppm (m, 1H); 2.03 ppm (m, 1H); 3.62 ppm (m, 1H); 3.80 ppm (m, 1H)

The mother liquor was heated to reflux and 1.2 L toluene was removed. The resulting solution cooled to room temperature, was seeded with the crystals collected in the earlier filtration, and stood for 12 hours (overnight). The crystals that formed were collected via vacuum filtration to give 60 g (after drying) of fine white crystals that were readily soluble in toluene.

The crystals were subjected to ring closure and the resulting ether had the same GC retention time as trans isomer of Grisalva. The stereochemistry of the diol collected and the ether formed were therefore tentatively assigned as:

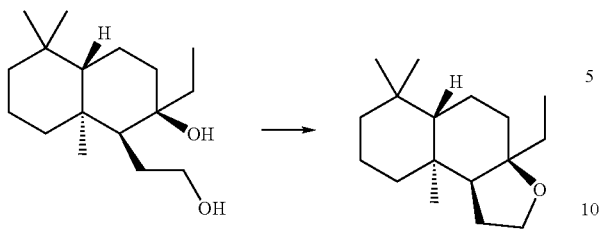

The trans isomer of Structure III possesses a woody, ambery ionone and strong fragrance notes.

HMNR 0.80 ppm (s, 3H); 0.89 ppm (t, 3H, J=6.5 Hz); 1.02 ppm (bd, 1H, J=13.5 Hz); 1.07 ppm (s, 3H); 1.11 ppm (s, 3H); 1.14 ppm (d, 1H, J=13.5 Hz, of t, J=4.4 Hz); 1.21 ppm (d, 1H, J=12 Hz, of d, J=4 Hz); 1.33 ppm (d, 1H, J=13 Hz, of t, J=4.5 Hz); 1.37 ppm (d, 1H, J=13 Hz, of q, J=4 Hz); 1.42 ppm (m, 1H); 1.49 ppm (m, 1H); 1.57 ppm (d, 1H, J=14 Hz, of t, J=4 Hz); 1.61 ppm (d, 1H, J=14 Hz, of q, J=6.5 Hz); 1.63 ppm (m, 1H); 1.66 ppm (bt, 1H, J=9 Hz); 1.67 ppm (m, 1H); 1.71 ppm (d, 1H, J=14 Hz, of q, J=6.5 Hz); 1.74 ppm (d, 1H, J=14 Hz, of t, J=4 Hz); 1.97 ppm (m, 1H); 2.07 ppm (m, 1H); 3.67 ppm (m, 1H); 3.82 ppm (m, 1H);

EXAMPLE II

Incorporation of 3a-Ethyl-6,6,9a-trimethyl-dodecahydro-napthol[2,1b]furan into a Fragrance Formulation

| | |
|---|---|
| Ambrettolide | 40 |
| Bicyclononalactone | 23 |
| Cashmeran ® | 15 |
| Damascone Delta | 1 |
| Dihydro Myrcenol | 50 |
| Ethylene Brassylate | 140 |
| Geranium Oil African | 6 |
| 3a-Ethyl-6,6,9a-trimethyl-dodecahydro-napthol[2,1-b]furan | 50 |
| Iso E Super ® | 325 |
| Kohinool ® | 50 |
| Lemon Oil | 55 |
| Linalool | 15 |
| Linalyl Acetate | 25 |
| Mandarin Oil Md LMR | 45 |
| Methyl Dihydro Jasmonate | 100 |
| Orange Oil | 20 |
| Sanjinol | 40 |
| TOTAL | 1000 |

This is a musky, citrus floral accord designed for alcoholic fragrances.

EXAMPLE III

Incorporation of (3aR,5aS,9aR,9bS)-3a-ethyl-6,6,9a-trimethyldodecahydronaphtho[2,1-b]furan into a Fragrance Formulation

| | |
|---|---|
| Triplal ® | 5 |
| Benzyl Salicylate | 55 |
| Bourgeonal | 30 |
| Citronellol | 15 |
| Cyclamal | 10 |
| Dihydro Myrcenol | 75 |
| Dimethyl Benzyl Carbinyl Acetate | 35 |
| Fleuramone | 8 |
| Floralozone | 4 |
| (3ar,5as,9ar,9bs)-3a-Ethyl-6,6,9a-Trimethyldodecahydronaphtho[2,1-B]Furan | 10 |
| Cis-3-Hexenyl Salicylate | 15 |
| Hexyl Cinnamic Aldehyde | 200 |
| Hexyl Salicylate | 60 |
| Lilial | 200 |
| Methyl Dihydro Jasmonate | 85 |
| Muskalactone | 30 |
| Orange Oil | 20 |
| Tetrahydro Myrcenol | 75 |
| Undecanal | 3 |
| Zenolide | 65 |
| Total | 1000 |

This is a floral, balsamic, ambery accord designed for alcoholic fragrances.

EXAMPLE IV

Incorporation of (3aR,5aS,9aS,9bS)-3a-ethyl-6,6,9a-trimethyldodecahydronaphtho[2,1-b]furan into a Fragrance Formulation

| Ingredient | Parts |
|---|---|
| (3ar,5as,9as,9bs)-3a-Ethyl-6,6,9a-Trimethyl-dodecahydronaphtho[2,1-B]Furan | 1 |
| Bornafix.Rtm | 3 |
| Citranalva | 1 |
| Cedrafix | 2.5 |
| Celestolide | 4 |
| Citrus Oil Distilled | 12 |
| Cyclacet | 3 |
| Dihydro Myrcenol | 40 |
| Fleuranil | 1 |
| Geranium Bourbon Oliffac | 0.5 |
| Hexyl Cinnamic Aldehyde | 4.5 |
| Iso E Super | 2.5 |
| Kharismal | 4 |
| Koavone | 1.5 |
| Linalyl Acetate | 5 |
| Phenoxanol | 5 |
| Precyclemone B | 1.5 |
| Pseudo Linalyl Acetate | 5 |
| Styralyl Acetate | 1 |
| Vigoflor | 1 |
| Zenolide | 1 |
| Total | 100 |

This is a citrus fragrance.

We claim:

1. A process for the preparation of an diastereoisomeric mixture of the following formula:

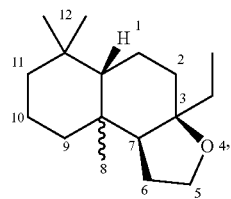

comprising the steps of:
(1) subjecting a compound of structure IV (IV)

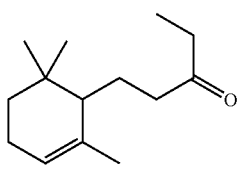

to Darzen's condensation to provide a compound of structure V (V)

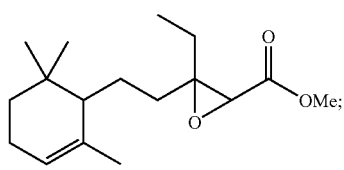

(2) saponifying the compound of structure V to provide a compound of structure VI (VI)

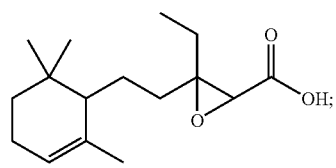

(3) subjecting the compound of structure VI to pyrolysis to provide a compound of structure VII (VII)

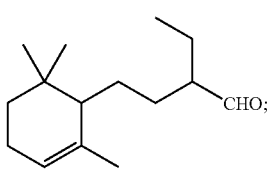

(4) subjecting a compound of structure VII to Knoevenagel reaction with cyanoacetic acid to provide a compound of structure VIII (VIII)

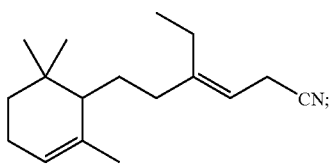

(5) providing a compound of structure IX by subjecting compound VIII to ring closing reaction (IX)

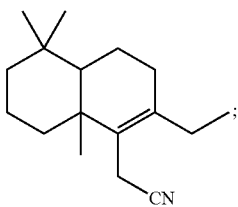

(6) saponifying the compound of structure IX to provide a compound of structure X (X)

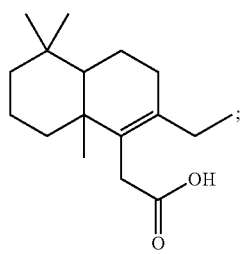

(7) cyclizing the compound of structure X to provide a compound of structure XI (XI)

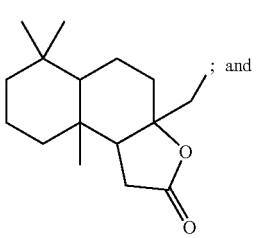

; and (8) reducing the compound of structure XI to provide a structure XII

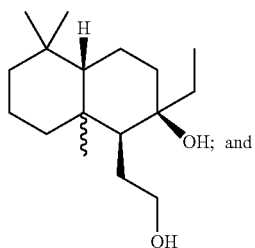
(XI)

(9) subjecting a diastereoisomeric mixture of the structure XII to ring closing reaction to provide the diastereoisomeric mixture of structure I:

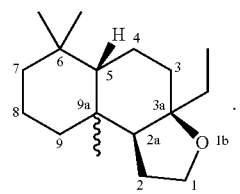

2. A process for the preparation of an isomeric component of the formula

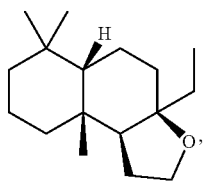

comprising the steps of:
(1) subjecting a compound of structure IV

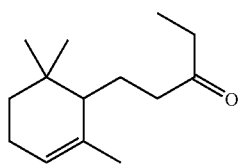
(IV)

to Darzen's condensation to provide a compound of structure V

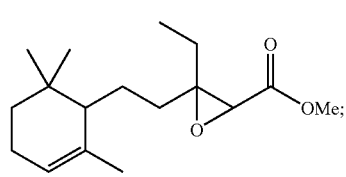
(V)

(2) saponifying the compound of structure V to provide a compound of structure VI

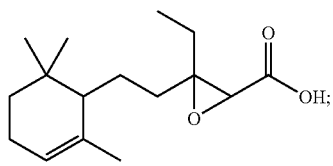
(VI)

(3) subjecting the structure VI to pyrolysis to provide a compound of structure VII

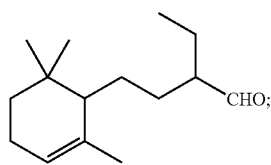
(VII)

(4) subjecting a compound of structure VII to Knoevenagel reaction with cyanoacetic acid to provide a compound of structure VIII

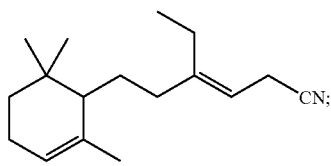
(VIII)

(5) providing a compound of structure IX by subjecting compound VIII to ring closing reaction

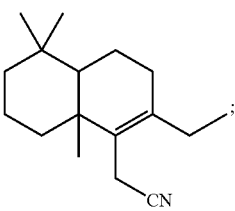
(VIII)

(6) saponifying the compound of structure IX to provide a compound of structure X

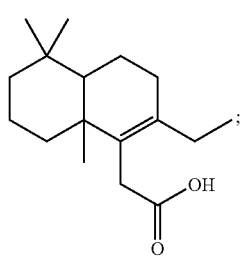
(X)

(7) cyclizing the compound of structure X to provide a compound of structure XI

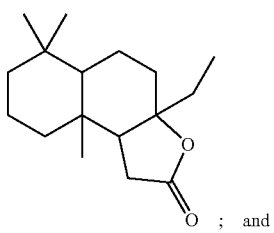
(X)

; and (8) reducing the compound of structure XI to provide structure XII

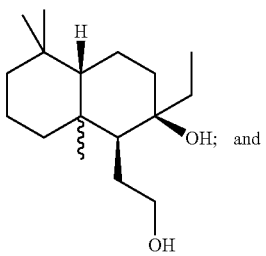
(XII)

OH; and

OH (9) crystallizing the compound of structure XII to form crystals and subjecting the crystals to a ring closure reaction and obtaining the cis isomer of Structure II:

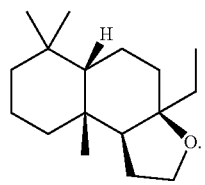

3. A process for the preparation of an isomeric component of the formula

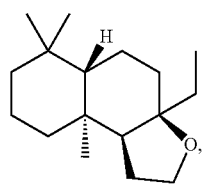

comprising the steps of:
(1) subjecting a compound of structure IV

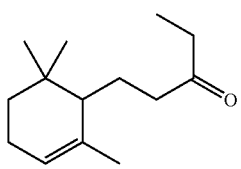
(IV)

to Darzen's condensation to provide a compound of structure V

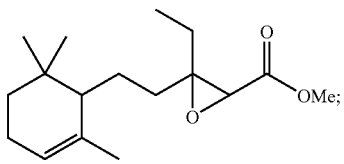
(V)

OMe;

(2) saponifying the compound of structure V to provide a compound of structure VI

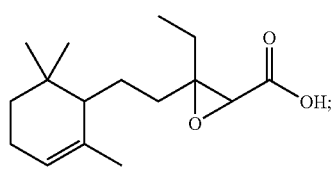
(VI)

OH;

(3) subjecting the compound of structure VI to pyrolysis to provide a compound of structure VII

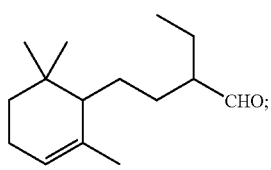
(VII)

CHO;

(4) subjecting a compound of structure VII to Knoevenagel reaction with cyanoacetic acid to provide a compound of structure VIII

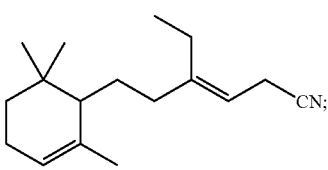
(VIII)

CN;

(5) providing a compound of structure IX by subjecting compound VIII to ring closing reaction

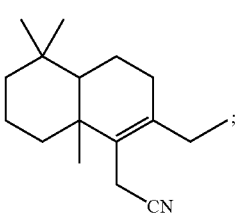

CN (6) saponifying the compound of structure IX to provide a compound of structure X

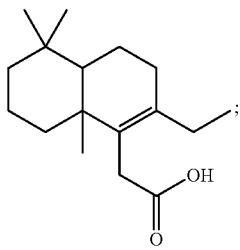
(X)

(7) cyclizing the compound of structure X to provide a compound of structure XI

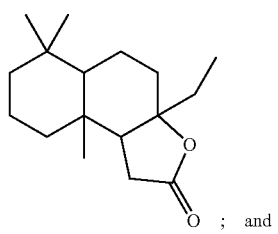
(XI)
; and (8) reducing the compound of structure XI to provide structure XII

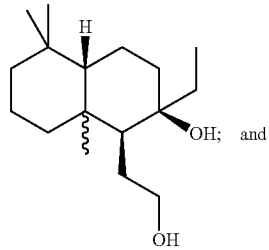
(XII)
; and (9) crystallizing the compound of structure XII to form crystals and subjecting the crystals to a ring closure reaction and obtaining the trans isomer of Structure III:

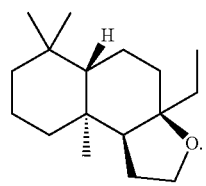

\* \* \* \* \*